United States Patent
Fahl

(10) Patent No.: US 10,052,446 B2
(45) Date of Patent: Aug. 21, 2018

(54) SPEECH VALVE WITH A COVER ELEMENT, COMPRISING A PISTON-SHAPED CLOSURE ELEMENT

(71) Applicant: Andreas Fahl Medizintechnik-Vertrieb GmbH, Cologne (DE)

(72) Inventor: Andreas Fahl, Köln (DE)

(73) Assignee: Andreas Fahl Medizintechnik—Vertrieb GmbH, Cologne (DE)

( * ) Notice: Subject to any disclaimer, the term of this patent is extended or adjusted under 35 U.S.C. 154(b) by 0 days.

(21) Appl. No.: 15/238,237

(22) Filed: Aug. 16, 2016

(65) Prior Publication Data

US 2016/0354569 A1 Dec. 8, 2016

Related U.S. Application Data

(63) Continuation of application No. PCT/EP2015/000314, filed on Feb. 13, 2015.

(30) Foreign Application Priority Data

Feb. 18, 2014 (DE) .......................... 10 2014 002 064

(51) Int. Cl.
*A61M 16/04* (2006.01)
*A61F 2/20* (2006.01)
*A61M 16/10* (2006.01)

(52) U.S. Cl.
CPC .......... *A61M 16/0468* (2013.01); *A61F 2/20* (2013.01); *A61M 16/047* (2013.01); *A61M 16/105* (2013.01); *A61M 16/1045* (2013.01); *A61F 2002/206* (2013.01)

(58) Field of Classification Search
CPC ..... A61F 2/20; A61F 2002/206; A61M 16/04; A61M 16/0468; A61M 16/047; A61M 16/1045
See application file for complete search history.

(56) References Cited

U.S. PATENT DOCUMENTS

| | | | |
|---|---|---|---|
| 4,582,058 A | 4/1986 | Depel et al. | |
| 2013/0192602 A1* | 8/2013 | Leibitzki | A61M 16/0468 128/205.27 |
| 2014/0150779 A1* | 6/2014 | Persson | A61M 16/1055 128/201.13 |

FOREIGN PATENT DOCUMENTS

| | | |
|---|---|---|
| DE | 69920440 T2 | 10/2005 |
| DE | 102010048317 A1 | 4/2012 |
| DE | 202012001825 U1 | 4/2012 |
| DE | 202013001950 U1 | 3/2013 |
| DE | 202013008092 U1 | 10/2013 |

(Continued)

OTHER PUBLICATIONS

International Search Report dated May 20, 2015, International Application No. PCT/EP2015/000314, filed Feb. 13, 2015.

*Primary Examiner* — Thomas J Sweet
*Assistant Examiner* — Daniel Bissing
(74) *Attorney, Agent, or Firm* — Dinsmore & Shohl LLP

(57) ABSTRACT

The invention relates to a speech valve for laryngectomy or tracheotomy patients, comprising a cover element, a housing part and a filter, the cover element comprising a piston-shaped closure element and said closure element being connected to the cover element to form one piece therewith. The cover element comprises an elastic material and by deforming at least part of the cover element the closure element closes the speech valve distally of the filter.

19 Claims, 5 Drawing Sheets

(56) References Cited

FOREIGN PATENT DOCUMENTS

EP    1077658  A1   2/2001
WO    9517138  A1   6/1995

* cited by examiner

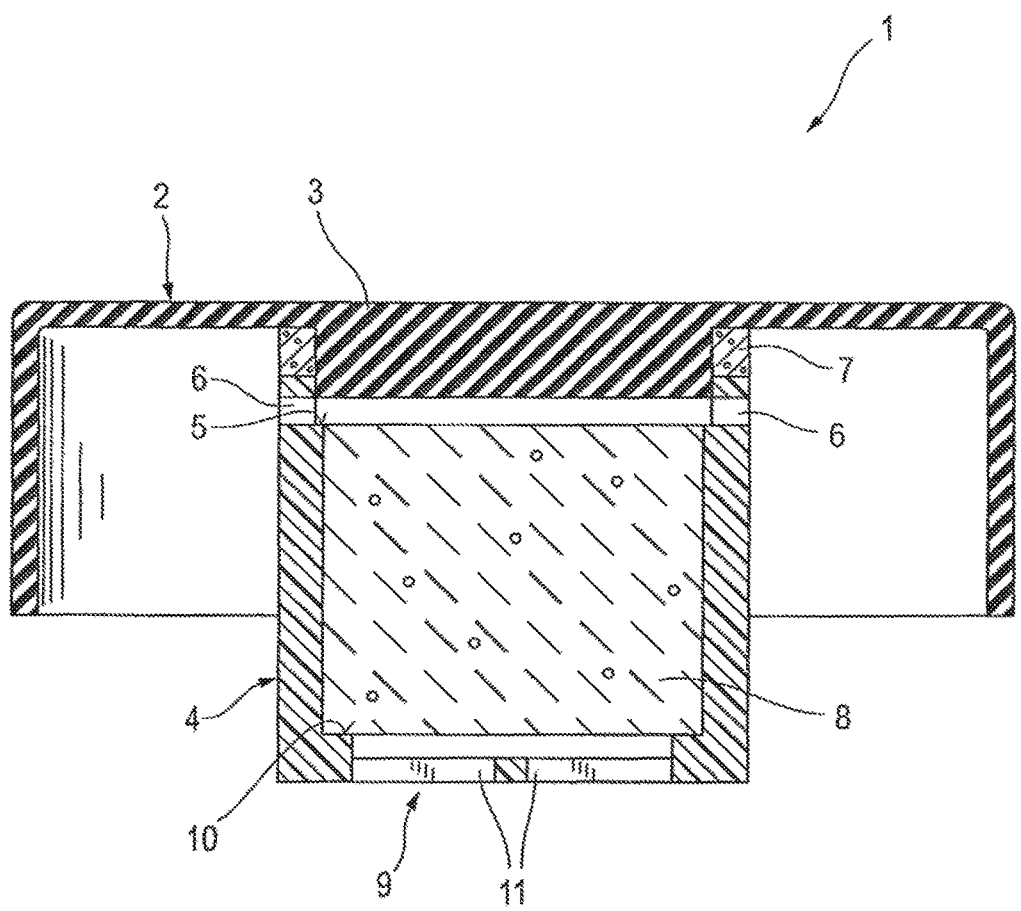

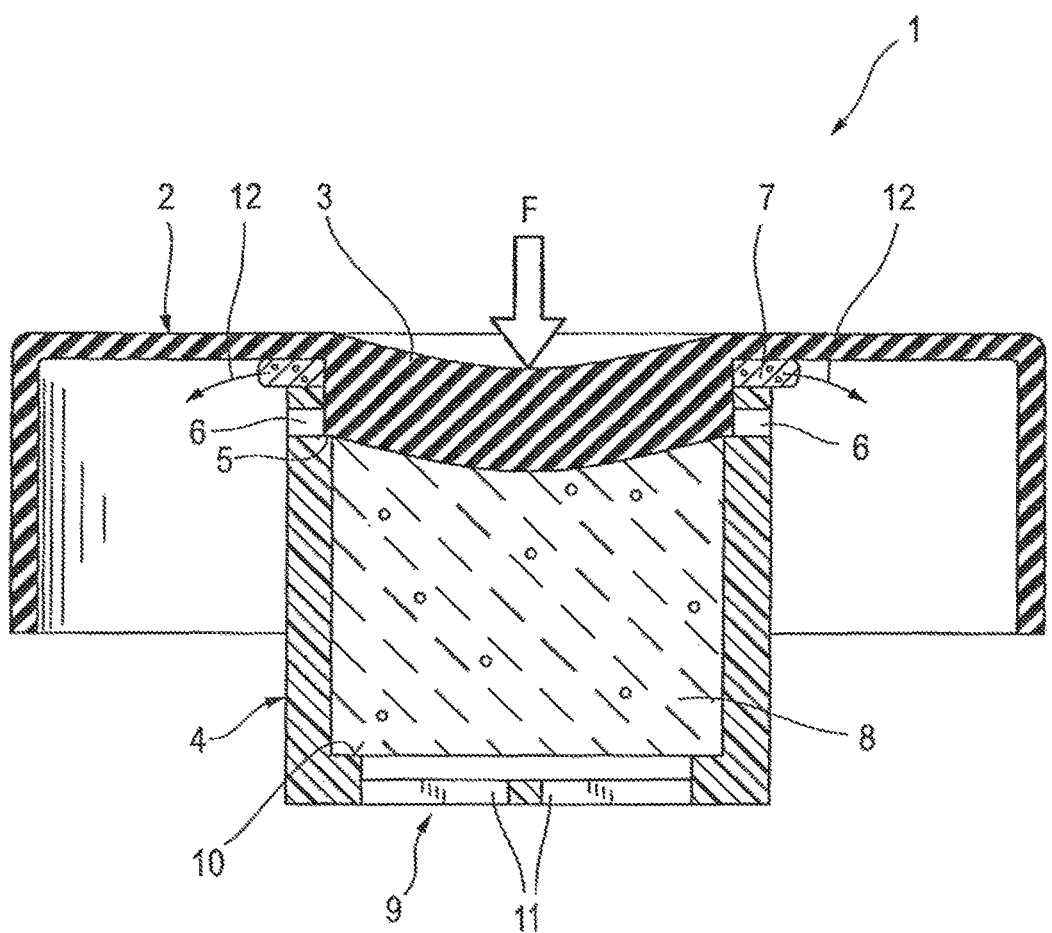

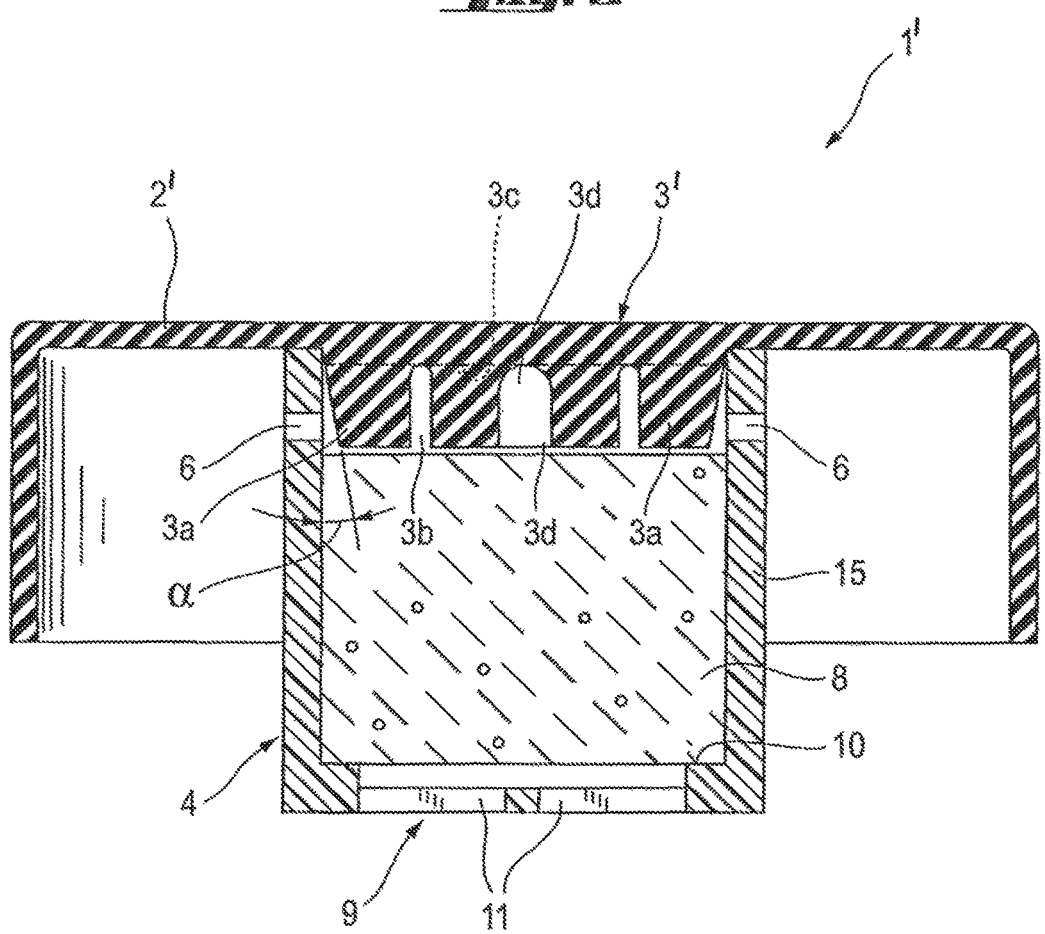

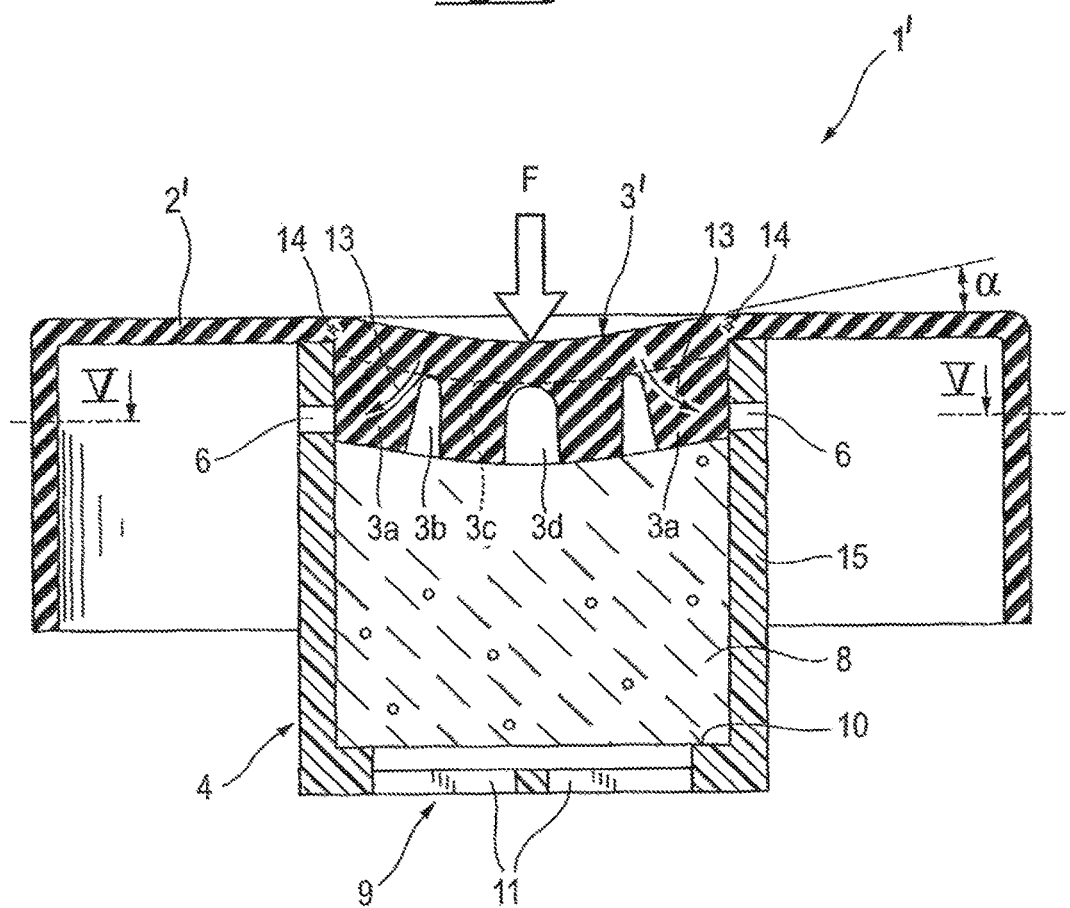

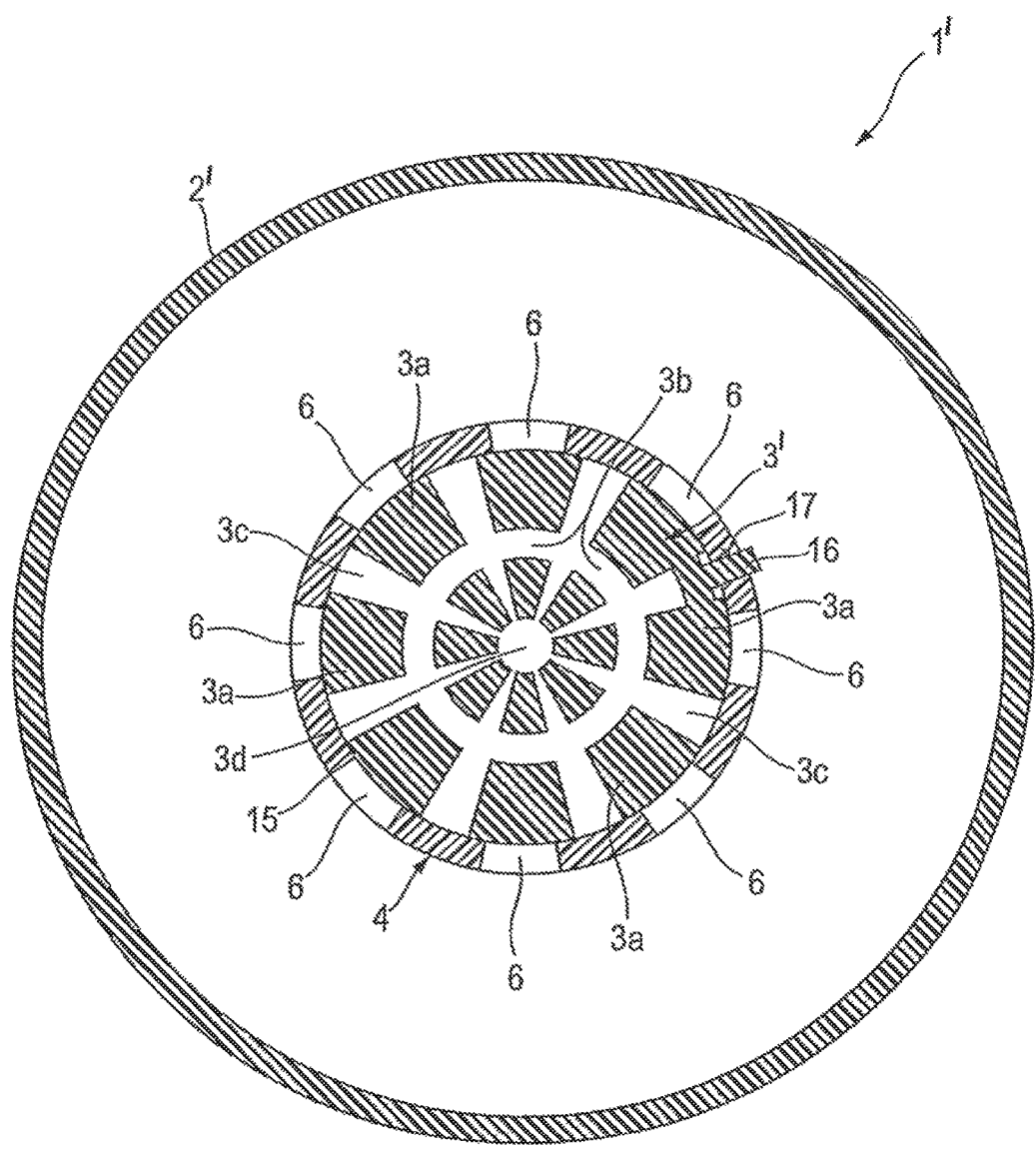

SPEECH VALVE WITH A COVER ELEMENT, COMPRISING A PISTON-SHAPED CLOSURE ELEMENT

CROSS-REFERENCE TO RELATED APPLICATIONS

This application is a continuation of PCT/EP2015/000314 filed Feb. 13, 2015, which claims priority of German Patent Application 10 2014 002 064.9 filed Feb. 18, 2014.

FIELD OF THE INVENTION

The invention relates to a speech valve for laryngectomy or tracheotomy patients. The speech valve has a cover element, a housing part and a filter.

BACKGROUND OF THE INVENTION

Speech valves are known from the prior art. These are attached, e.g. to a tracheostoma cannula or a tracheostoma bandage, so that people without vocal chords can speak by means of a voice prosthesis. By actuating the speech valve, air is conducted through a voice prosthesis, which is disposed in a fistula between the trachea and the esophagus. If the vocal chords are still present, the air must not escape the tracheal cannula before it reaches the vocal chords.

A speech valve is known from U.S. Pat. No. 4,582,058A, which can be closed by means of a pressure impulse resulting from the respiration of the patient, thus enabling the patient to speak. Unfortunately, these valves have not proven to be particularly reliable.

WO 95/17138 A proposes that the speech valve be combined with an artificial nose. This artificial nose is a filter that traps the moisture and heat in the exhaled air, and moistens and heats the air flowing into the tracheal cannula.

EP 1 077 658 B1 describes a voice valve having a filter, wherein the voice valve has an elastic housing, or an elastic valve element, respectively, and the housing, or valve element can be deformed, e.g. by means of finger pressure, such that a housing part bears on a valve seat, and the valve is closed thereby.

SUMMARY OF THE INVENTION

The object of the present invention is to provide a speech valve, that has a simple construction and is economical to produce.

The object shall be achieved according to the invention by means of a speech vale according to Claim 1. Further advantageous designs can be derived from the following description, the drawings and the dependent Claims. The individual features of the designs described herein are not limited thereto, but rather, can be linked to one another and to other features for further designs.

A speech valve for laryngectomy or tracheotomy patients is proposed. The speech valve comprises a cover element, a housing part and a filter. Furthermore, the cover element comprises a piston-shaped closure element, wherein the closure element is connected in an integral manner to the cover element. The closure element is advantageously entirely disposed in an interior formed by the housing part. The cover element furthermore comprises an elastic material, having, in particular, rubbery elastic properties, wherein, by means of deformation, in particular an indentation toward at least a proximal region of the cover element, the speech valve closes the filter at the distal end. Advantageously, the cover element, the filter and/or the housing can be separated from one another, such that the cover element or the filter are designed in particular such that they can be replaced. The cover element, filter and housing part are thus separate components in accordance with an advantageous embodiment. The reset forces that are necessary for transferring the speech valve from a closed setting, necessary for speaking, to an open setting, are substantially, advantageously substantially entirely, preferably entirely, provided by the cover element formed from an elastic material. As a result, otherwise necessary reset means, such as springs or suchlike, are advantageously eliminated. Because, as a result of the distal closing, the filter is in any case only slightly, in particular substantially in only a sub-region disposed above a valve seat provided by the housing part, preferably substantially not compressed, its functionality for heat and moisture exchange remains as good as fully intact, if not fully intact.

The directional information used herein are, in accordance with the invention, to be understood with respect to the intended installation on a body, or, respectively, on a tracheal cannula or a tracheostoma bandage.

The term "distal" as set forth in the present invention in relation to a feature of the device according to the invention pertains to an arrangement or use of said feature at a distance, or facing away, or lying opposite a tracheostoma bandage or a tracheal cannula, in general a skin surface of a person, in particular wearing such attachment means for the device according to the invention. A closure distal to the filter, i.e. in transferring the closure element from an open setting into a closed setting, means that the filter is disposed entirely beneath the closure element, i.e. proximal thereto. The term "proximal" as set forth in the present invention in relation to a feature of the device according to the invention refers to an arrangement or use thereof in the vicinity or facing toward, or adjacent to a tracheostoma bandage or a tracheal cannula, in general a skin surface of a person, in particular wearing such attachment means for the device according to the invention.

The term "piston-shaped" with respect to the closure element is to be understood in this context to mean that the closure element extends in the housing part in the vertical direction, beyond a partial height thereof, and that, by means of the piston, a closed setting of the speech valve can be obtained in order to generate speech. As a result of the piston-shaped design, the path between the undersurface of the closure element, or the undersurface of the cover element and the valve seat, respectively, is preferably shortened. Piston-shaped as set forth in the present invention does not mean in particular that a vertical extension of the closure element is greater than a horizontal extension thereof.

"Integral" as set forth in the present invention does not mean that the closure element and the cover element must be made of the same material. They can be made, for example, from different materials, and connected to one another, e.g. with adhesive, using mechanical means, etc. In this case as well, the two elements collectively form a single component of the speech valve according to the invention, which is to be referred to as integral as set forth in the present invention.

The proposed speech valve has the advantage that very few components are used in creating the speech valve. A further major advantage of the proposed speech valve is that the filter is not, or is only insubstantially, compressed when the speech valve is closed. The compression of the filter in the artificial nose or speech valves known from the prior art has the disadvantage that the filter is wrung out, and thus sacrifices its moisture. Furthermore, there is fundamentally the risk that the filter material will be pushed into the tracheal cannula, and in the worst case, inhaled by the user.

It is provided in one design that the housing part comprises a distal valve seat, wherein the closure element interacts with the valve seat, in particular via its undersurface, when the speech valve is actuated. Advantageously, the speech valve and the valve seat interact such that the valve closes. The actual valve is formed by a piston-shaped closure element, or a piston and the valve seat, respectively. The valve seat is preferably disposed in the interior of the housing part.

It is provided in an advantageous embodiment that the housing part comprises inflow openings, distal to the valve seat. This has the advantage that the inflowing air during inhalation flows entirely through the filter disposed in the housing part, before it flows further through the at least one discharge opening into, e.g. a tracheal cannula, or the trachea, respectively. The valve seat is advantageously disposed on the same plane as the distal end of the filter, but it can also be disposed above or below the distal end of the filter. When it is disposed beneath the distal end of the filter, the filter, substantially the excess part of the filter, is compressed slightly, when the speech valve is transferred from an open setting into a closed setting. In another design, it is provided that the valve seat is spaced distally apart from the surface of the filter. Another variation provides that the valve seat is disposed in the housing such that it is spaced proximally to the distal end of the filter, such that when the speech valve is closed, the piston partially compresses the filter.

The, in particular partial, compression of the filter during the closing process shall be explained in greater detail below.

It is provided in another embodiment that the housing part comprises inflow openings, which can be closed by means of the closure element when the speech valve is actuated. In particular, the piston is inserted into the housing such that it blocks the passage of air at the inflow openings from inside the housing, at least in part, when the speech valve is actuated. The speech valve is thus closed in this embodiment by alternating, or collectively acting closure mechanisms: on one hand, the piston blocks, at least partially, the passage of air though the inflow opening. Furthermore, the piston is designed such that it interacts with the valve seat or the filter, when it is pushed into the housing part, such that a blockage of the air flow inside the housing is implemented. Another closure method is to place the piston, preferably entirely, on the surface of the filter, in particular when there is no valve seat, although it may be the case that it preferably extends beyond an outer circumference of the filter when it has been inserted, such that a passage of air through the filter is substantially prevented. This has the advantage that a sealing of the speech valve can be reliably obtained. One or more openings may be provided, alternatively or additionally, in the region of the closure element, in particular a central region, in order for air to be able to flow through the valve. These are closed when the valve is closed, in particular by means of a finger of the user.

According to another embodiment, it is provided that the cover element is releasably disposed on the housing part. By way of example, different cover elements may be provided for a housing part, having different properties, e.g. in terms of material, stability and/or shape. Furthermore, for decorative purposes, different colors and decorations may be provided on the cover element, such that a variable design option is obtained for the speech valve, and thus the tracheostoma.

There are, however, other possibilities for a releasable connection, e.g. provided by one or more Velcro or adhesive connections. The latching connection can be designed such that the cover element has two, three, four, or more latching elements, e.g. in the form of lugs, which are disposed on an inner surface of the cover element, allocated to the side walls of the housing part. It may be provided thereby that the latching elements encompass an upper edge of the housing part, in a region thereof in which inflow openings are provided. Corresponding receivers or recesses, or even breaks, may be provided on this edge, in which the latching elements of the cover element engage. Conversely, appropriate latching elements can also be disposed in the distal end region of the housing part, e.g. lugs, which engage in corresponding recesses, disposed on the undersurface of the cover element. The releasable connection between the cover element and the housing part is preferably designed such that no air can enter or escape between the cover element and the housing part in the connecting region. It may be provided, for example, that three or four lugs are disposed on the inside of the cover element, which in turn are disposed on the flange or bulge disposed on the inside of the cover element, corresponding in terms of its size, i.e. in particular its diameter, to the diameter of the housing part, and basically covering the upper edge of the side walls of the housing part. The latching elements, or lugs, preferably engage in corresponding recesses on the upper edge of the cover element, or conversely, latching elements or lugs on the upper edge of the cover element could engage in the recesses. The bulge or flange can be disposed spaced only slightly apart from a vertical edge of the cover element, to the extent that the cover element only extends over a side wall of the housing part. The cover element can, however, be riveted or screwed to the housing part, or it can be connected to the housing part in the manner of a bayonet joint.

Another variation provides that the cover element is screwed onto the housing part. Furthermore, one design provides that the cover element is attached to the housing part by means of a bayonet joint. Another variation may be provided in which the cover element is glued or welded to the housing part.

The different adjustment possibilities, e.g. in terms of the elasticity of the material, in particular the rubbery elastic material, or in the shaping thereof, could affect different technical properties of the speech valve. Thus, for example, the reset force can be influenced by the thickness of the material for the cover element, as well as the shape thereof. It is provided in one design that differently adjusted cover elements are provided, which are disposed on the housing part such that they can be exchanged, and can be used for different applications.

According to the invention, the cover element is made, at least in part, of an elastic material. Advantageously, the elastic material of the cover element is a rubbery elastic material. Preferably, the elastic material of the cover element is a linear-elastic material. Natural rubber or synthetic rubber, in particular butyl rubber, or ethylene propylene diene monomer rubber (EPDM), in particular, can also be used for the rubbery elastic material. The use of silicone materials, in particular medical silicone materials, is also possible. Fundamentally, the rubbery elastic material of the cover element can be an elastomer, e.g. a thermoelastic elastomer having an olefin or urethane base, particularly preferably an at least partially cross-linked thermoplastic elastomer having an olefin base, a polyester elastomer, a thermoplastic copolyester, a styrene block polymer, or a thermoplastic copolymer. Instead of it being made from a rubbery elastic material formed from a polymer, the cover element can be made at least in part from a linear-elastic material, in particular a metal having a sufficient elasticity. Other materials that provide sufficient elasticity, however, may also be used. It is particularly preferred that the cover element be made of an elastic, preferably rubbery elastic material, and furthermore contains no other materials. The cover element can have a uniform thickness thereby, although the thickness may be reduced, in particular in the region of a transition from a horizontal to a vertical extension of the cover element, and/or likewise in a region, in which a user transfers the speech valve from the open setting to the closed setting, and back, by means of a finger.

In a preferred design, it is provided that at least one elastic region of the cover element functions as the reset element. In accordance with one design, the elastic material of the cover element is a rubbery elastic material. If this is pressed inward, in order to displace the piston proximally inside the housing, and the thus to close the speech valve, the reset force inherent to the rubbery elastic material causes the speech valve to open again, as soon as the force applied to the cover element is reduced. Another design provides that the elastic material of the cover element is a linear elastic material, e.g. a metal. The cover element can be made from one or more materials. In particular, in one design it is provided that materials having different elastic properties are provided, and by way of example, the piston contains a different material, in particular a rigid, i.e. non-elastic material, than the rest of the cover element, which is preferably made, at least in part, of an elastic material. In another advantageous design, it is provided that the cover element, and thus also the closure element, are made of an elastic, furthermore preferably identical elastic, material. Preferably, the cover element can be produced together with the closure element in a single component injection process. When an identical elastic material is used, the elasticity of the cover element and the closure element can be affected, e.g. via the wall thicknesses or other mechanical means, such as beading or reinforcement strips, hollow spaces or other means, for example, such that they exhibit different elasticity modules, despite being made from the same material.

Furthermore, one design provides that the closure element comprises a rigid material, at least in part, meaning that a rigid or non-elastic material, in particular in the region of the surface, interacts with the valve seat. The use of a rigid material for the closure element has the advantage that it is not, or is only insubstantially, deformed during the actuation. In this manner, a complete closure of the speech valve can occur, even when the user does not press the cover element in the center, because the closure element is not forced into the housing part from the side, or in an uneven manner, resulting in a therefore insufficient closure. In another design it is provided that the rigidity of the closure element is obtained, or is adjusted thereby, by the use of a rubbery elastic solid. The closure element can be formed as an integral part of the cover element, in particular also being made of the same material. It is preferred, however, that the piston-shaped closure element is made from a material having a lower elasticity module, thus a more rigid, preferably more rigid, material than the cover element. It is particularly preferred that the piston-shaped closure element is provided with at least one recess or at least one projection on its surface facing the cover element. Conversely, it is preferred that at least one projection or at least one recess is provided on the undersurface of the cover element, facing the closure element. The recess and projection on the cover element and the closure element interact, e.g. by means of a form or force fit, in particular by means of adhesive or a mechanical engagement or suchlike, such that an integral component of the cover element and piston-shaped closure element is obtained, which elements are connected in an integral manner as set forth in the present application.

The cover element is advantageously formed in the manner of a hat or cap. This is to be understood to mean that the design of the cover element is such that the cover element extends at least in part, preferably entirely (i.e. toward all sides), over the side walls of the housing. The extension over the side walls of the housing is obtained thereby, advantageously, in a direction substantially parallel to a skin surface of the body. It is further preferred that the extension over the side walls of the housing is obtained in the vertical direction, i.e. in the direction of the vertical extension of the housing part from its proximal end to its distal end. The vertical extension preferably occurs over a partial length of the vertical extension of the housing part. The cover element can also have openings in the region extending over the side walls of the housing part, formed in particular in the manner of slots. Openings can also, however, be disposed in the deformation region of the cover element, in particular, precisely one opening, which is closed when the user transfers it to the closed setting. This design is provided, in particular, then when the closure means is not fully or partially connected to the undersurface of the cover element at its upper surface, which faces toward the undersurface of the cover element, which is not possible, but rather, in particular, is somewhat spaced apart therefrom, e.g. by means of a type of attachment cross, in which at least one recess or at least one projection is provided at the intersection thereof, for attachment to the undersurface of the cover element. The cover element can have at least one projection or at least one recess on its undersurface, which interacts with the corresponding means on the closure element. By way of example, the projection can be designed in the shape of a pin or a rod, and the recess can be designed as a blind hole, preferably adapted to the projection. Preferably, there is a form or force fit connection between the cover element and the closure element. The attachment cross is than disposed on a cylindrical section, which forms the actual piston. The cylindrical section is advantageously designed as a circular plate having a certain thickness, or vertical extension.

Advantageously, the cover element exhibits a height, from the proximal to the distal end, with respect to the ends of the housing part, which is at least 30% to approx. 90%, preferably approx. 40% to approx. 95%, more preferably approx. 50% to approx. 95%, yet more preferably approx. 70% to approx. 95%, yet more preferably approx. 80% to approx. 90% of the of the housing part. The cover element preferably has a height, from the proximal end to the distal end, that is a maximum of approx. 95%, more preferably a maximum of approx. 90%, yet more preferably a maximum of approx. 80% of the height of the housing part, determined starting from the proximal lower edge facing toward the body, to the distal upper edge, facing away from the body, of the side walls thereof.

The height of the cover element form the proximal end to the distal end is determined, on one hand, by the cervical edge, and on the other hand, by the distal upper surface thereof, which projects furthest away from the tracheostoma.

To the extent that the term "approx." is used in the present invention, this is to be understood to mean that there is a tolerance range that is regarded as typical by the person skilled in the art in the present field, in particular a tolerance range of ±20%, preferably ±10%, more preferably ±5%, in each case in relation to the value under consideration.

In one preferred embodiment, the cover element extends both laterally as well as vertically beyond the housing part. More preferably, the cover element comprises a cervical edge. The cervical edge, which faces toward the throat of a wearer of the speech valve according to the invention, is preferably rounded, such that it does not cause skin irritation when there is skin contact while the user is moving. In particular, the cover element has a round, oval, or otherwise rounded or rectangular shape, viewed laterally, wherein, with a rectangular shape, the corners are advantageously rounded. Advantageously, all of the edges of the cover element are rounded, in order to prevent injuries or skin irritation, in particular.

One advantage of the features described above in conjunction with the design of the cover element is a guidance of the air along the throat during inhalation, such that the air is pre-heated before it enters the interior of the speech valve, and in particular the filter. Depending on the design of the cover element, in particular with respect to the arrangement of the cervical edge being more proximal to the side walls of the housing part, or more distal thereto, as well as by the arrangement of the cover element having the cervical edge such that the cervical edge is close to, or somewhat further away from, the throat of the user, both the volume of the air flow that is to be received, as well as the pre-heating thereof, can be adjusted.

It is particularly advantageous thereby when the cover element does not have an opening at the distal end, in particular in a central region facing toward the housing part, that enables a passage of air through the filter from the distal end to the proximal end. The housing part then preferably comprises one or more inflow openings in a side walls thereof. By this means, it is ensured that the air is substantially guided along the throat, before it enters the housing part. Alternatively or additionally, it can also be provided, however, that the cover element has at least one distal opening, in particular in a region facing the interior of the housing part. As a result of the at least one distal opening, at least a portion of the inhaled air can enter the housing, or pass through the filter, directly, such that the air can enter the trachea, or the tracheal cannula in a moistened and heated state.

In another variation of the speech valve, it is provided that the filter is disposed in the housing part with an excess tolerance or a transition tolerance. Advantageously, according to one design, the filter has no play in the housing. This prevents inhaled and exhaled air from bypassing the filter. Furthermore, the filter that has been fit in this manner has the advantage that it will not be displaced in the housing as a result of changing air pressure. It is, however, also possible to dispose the filter in the housing such that a gap is formed between the outer wall and the inner wall of the housing part. The filter can be retained by means of a housing part using adhesive or suchlike, but it can also be held in place merely by the tight fit. Retaining means could also be disposed on the inner wall of the housing part, which are able to penetrate the filter material. These could be designed as truncated cone-shaped projections. Any other design for the retaining means is also possible, as long as it ensures a retention of the filter in the housing part.

In another preferred embodiment it is provided that the filter comprises an airtight skin at least at its distal end, at least in sections. By way of example, by providing an airtight skin in accordance with one embodiment, there is no need to provide a valve seat in the housing. If, for example, the closure element is bowed in an elastic manner when the speech valve is actuated, such that it does not bear in its entirety on the filter, the airtight skin can be disposed on the distal end of the filter such that it consequently interacts with the closure element and causes a full closure of the speech valve. Advantageously, it is provided according to one design, that the airtight skin is disposed in an annular manner on the distal end of the filter. In another advantageous design, it is provided that at least in the region of the distal end of the filter, comprising no skin, it can then be closed by means of the closure element.

Furthermore, it is provided in one embodiment that the filter is partially compressed by the actuation of the speech valve. During a closure thereof, a partial compression of the filter may occur in one design inadvertently or intentionally, or as a result of the tolerances of the speech valve. The speech valve is designed such that a compression approx. 0% by volume to approx. 50% by volume, in particular approx. 1% by volume to approx. 25% by volume, preferably approx. 1% by volume to approx. 50% by volume, more preferably approx. 1% by volume to approx. 10% by volume, particularly preferably approx. 1% by volume to approx. 5% by volume is provided for. The compression can be adjusted, for example, by the cover material or by the geometry of the cover. By this means the user is informed when it is no longer necessary to continue pressing by the normal amount of force that is exerted, e.g. approx. 5 N to approx. 15 N. If the user attempts to press the cover element further inward, this normally results in discomfort as a result of the pressure applied to the tracheostoma, or the surrounding tissue or the tracheal cannula. The speech valve is designed such that it already closes before the normally exerted force of, e.g., approx. 5 N to approx. 15 N has been reached. Furthermore, the setting of the compression of the filter can be adjusted by the provision of the valve seat. It is provided in another design that a compression of the filter is limited by means of a counter bearing disposed on or in the housing part. Preferably, the closure element can only be pushed into the speech valve as far as the counter bearing. The provision of a counter bearing prevents the filter from being pushed into the tracheal cannula, and thus prevents a respiration of the filter. Furthermore, a squeezing of the moisture out of the filter is reduced or prevented by the only limited compression. The counter bearing can be implemented, for example, as a rod or wall, which extends through the filter from the proximal end toward the distal end, and is disposed on the housing in any arbitrary shape. Another possible design provides that the counter bearing is designed as an at least partially encircling edge, which is preferably not identical to the valve seat.

BRIEF DESCRIPTION OF THE DRAWINGS

Further advantageous designs can be derived from the following drawings. The illustrations depicted there are not to be regarded, however, as limiting, but rather, the features described therein can be combined with one another and with the features described above to obtain further designs. Moreover, it should be noted that the reference symbols given in the descriptions of the figures do not limit the scope of protection for the present invention, but merely refer to the exemplary embodiments indicated in the figures. Therein:

FIG. 1 shows a speech valve in a first embodiment, in a side view, in the un-actuated state; and FIG. 2 shows the speech valve according to FIG. 1, in a side view, in the actuated state;

FIG. 3 shows a speech valve in a second embodiment, in a side view, in the un-actuated state;

FIG. 4 shows the speech valve according to FIG. 3 in a side view, in the actuated state; and FIG. 5 shows a sectional view along the cut V-V according to FIG. 4.

DETAILED DESCRIPTION OF THE PREFERRED EMBODIMENTS

FIG. 1 shows a speech valve 1 for laryngectomy or tracheotomy patients, having a cover element 2, a housing part 4, and a filter 8. The cover element 2 comprises a piston-shaped closure element 3, which is connected to the cover element 2. In the design shown here, the cover element 2 is made entirely of one material, in particular silicone. The cover element 2 is disposed on the distal end of the housing part 4. Preferably a latching connection, not shown in detail here, is provided, in order to attach the cover element 2 to the housing part 4. In an alternative design, it is provided that the cover element 2 is clamped to the housing part 4 by the tight fit of the closure element in the housing part 4, or is connected thereto by adhesive. In the proximity of the closure element 3, inflow openings 6 are provided in the side walls of the housing part 4, which enable an inflow of air. A discharge opening 9 is provided at the proximal end of the housing part 4, which enables a discharge of the inhaled air in the tracheal cannula, or the tracheostoma, during inhalation. A valve seat 5 is formed by the side walls of the housing part 4, as an encompassing projection in the form of a cross section narrowing.

The filter 8, which is disposed with a precise fit in the housing part 4, moistens the inflowing air, before this air reaches the tracheal cannula or the tracheostoma. A filter seat is disposed in the housing part 4 at the proximal end, which prevents a slipping of the filter into the tracheal cannula, or the trachea. Furthermore, the embodiment shown here provides that a support cross 11 is provided, which likewise prevents the ingress of foreign bodies, in particular the filter 8, into the trachea.

Furthermore, an elastic suspension 7 is disposed at the distal end of the housing part 4, which can be formed, for example, from an open-pore or closed-pore foam material, or some other elastic material. The elastic suspension 7 is preferably connected to the housing part 4 in an integral manner, and can be produced therewith, for example, by means of a two-component injection molding. An elastic suspension 7 can be provided, as a rule, in all of the embodiments described in the present invention, but this is not necessary. The provision of an elastic suspension 7 depends on the design of the cover element 2 with the closure element 3, and the material from which it is formed. It may not be necessary to provide an elastic suspension 7. FIG. 2 shows the speech valve in the actuated state. A force F, normally exerted by means of finger pressure applied to the cover element 2 of the speech valve 1, deforms the cover element 2 such that the closure element 3 is moved into the housing part 4. The closure element preferably bears with its entire surface on the filter 8. It can furthermore be seen that the inflow openings 6 are closed inside the housing part 4 by the closure element 3. It can also be seen that the closure element 3 rests on the valve seat 5 circumferentially.

In the closed setting of the speech valve 1 shown in FIG. 2, it is visible that the elastic suspension 7 is compressed, wherein material thereof is displaced in the direction of the arrow 12, and extends over an outer contour of the housing part 4 thereby.

FIG. 3 shows a speech valve 1' in another, alternative design. Identical features are indicated with the identical reference symbols thereby, as those used in FIGS. 1 and 2. The housing part 4 according to FIG. 3 is substantially identical to that in the first embodiment according to FIGS. 1 and 2, but no elastic suspension 7 is provided. The embodiment in FIG. 3 is substantially distinguished from the first embodiment according to FIGS. 1 and 2, with regard to the design for the cover element 2, or the closure element 3, by the design of a cover element 2' and a closure element 3', which is designed in the manner of a piston. The piston-shaped closure element 3' has valve closure flaps 3a disposed at its proximal end, encompassing this in the shape of a star (see FIG. 5 as well). These are formed, in relation to an inner contour of the housing part 4, or the inner wall of the housing part 4, respectively, with an angel $\alpha$ opening toward the proximal end. As a result, it is possible that the lateral surfaces of the valve closure flaps 3a facing toward the inner wall of the housing part 4, lean against the inner wall of the housing part 4 when transferred to the closed setting (see FIG. 4), and close the inflow openings 6 as a result. These inflow openings 6 are preferably disposed such that they are distributed uniformly about the circumference of the housing part 4, and are separated thereby by means of struts formed by the housing part 4. These struts formed by the housing part 4, in turn, are assigned to rounded notches 3c, which allows the piston-shaped closure element 3' to move when a force F is exerted during the transference to the closed setting.

Furthermore, at least one cylindrical notch 3b is provided in the cross section of the piston-shaped closure element 3', which is disposed concentrically around a central, blind hole-shaped recess 3d, and which likewise serves as a bearing for the outer wall of the valve closure flaps 3a on the inner wall of the housing part 4. The angle $\alpha$ can furthermore be derived from FIG. 3, which can be referred to as the pivot angle, and refers to the valve closure flaps 3a, which cover the inflow openings 6 when transferred into the closed setting after exerting a force F, as shown in FIG. 4.

FIG. 4 shows the second embodiment according to FIG. 3, in the closed setting after exertion of a force F, wherein, in particular, the pivoting of the valve closure flaps 3a in the direction of the arrows 13 and the bearing of the outer wall of the valve closure flaps 3a on the inner wall of the housing part 4 obtained thereby, is illustrated. The piston-shaped closure element 3' then bears entirely on the distal upper surface of the filter 8, which is minimally compressed thereby.

In the embodiment according to FIGS. 3 to 5, the valve 5 is no longer needed, or the bearing of the outer wall of the valve closure flaps 3a on the inner wall of the housing part 4 can be referred to as the valve seat, because the inflow openings 6 are closed by this means. Consequently, the present invention is not limited to those speech valves having a typical valve seat, as is shown in the first embodiment according to FIGS. 1 and 2. As set forth in the present invention, the cover element 2 can, in general, have notches of any type that allow movement on the part of the closure element 3 in the region of the piston-shaped closure element 3. The embodiment shown in FIGS. 3 to 5 is merely exemplary in this regard. The cover element 2 with the closure element 3 in accordance with the first embodiment can, for example, have the recess 3d and notches 3b formed in the manner of blind holes.

FIG. 5 shows the second embodiment of the speech valve 1' cut along the line V-V in FIG. 4. The arrangement of the radially encircling inflow openings 6, interrupted by the struts formed by the housing part 4, can be seen particularly well thereby, as is the case with the assignment of the valve closure flaps 3a to the inflow openings 6. Likewise, the design of the central, blind-hole-shaped recess 3d and the notches 3b, disposed concentric thereto, are visible. The sectorial notches 3c can also be discerned. A latching of the cover element 2' to the piston-shaped closure element 3' can also be derived from FIG. 5, which is implemented in that a positioning tappet 16, disposed on the outer circumference of the piston-shaped closure element 3', engages in a positioning slot 17 in a strut formed by the housing part 4, between two inflow openings 6. As a result, the cover element 2' is secured against rotation, as well as being held in place, in the speech valve 1'. The design of the positioning slot 17 and the positioning tappet 16 can be such that a latching is also provided thereby, which likewise enables a removal of the cover element 2', formed as an integral unit, from the housing part 4.

By means of the specified measures, but also individually in and of themselves, a secure sealing of the speech valve 1 is obtained in a simple manner. A reset force is contingent on the selection of the material, the shape, and the cover element, and can be adjusted. If the force to the cover element is released, or the user releases the cover element, this reset force leads to a re-opening of the valve.

The invention claimed is:

1. A speech valve for laryngectomy or tracheotomy patients comprising: a cover element, a housing part and a filter, wherein the cover element has a piston-shaped closure element, the closure element being connected to the cover element in a monolithic manner, wherein the cover element is formed of an elastic material, the housing part having a valve seat at a distal end of the housing, the piston shaped closure element spaced apart from the valve seat and a distal end of the filter when the valve is in an open position and wherein the closure element contacts the valve seat to close the speech valve at the distal end to the filter through deformation of at least a region of the cover element.

2. The speech valve of claim 1, further comprising: the housing part has inflow openings distal to the valve seat.

3. The speech valve of claim 2, further comprising: the housing part has inflow openings at the distal end of the filter.

4. The speech valve of claim 3, further comprising: the housing part has inflow openings, which can be closed by means of the closure element when the speech valve is actuated.

5. The speech valve of claim 1, further comprising: the cover element is releasably disposed on the housing part.

6. The speech valve of claim 1, further comprising: the cover element is disposed on the housing part by means of a latching connection.

7. The speech valve of claim 1, further comprising: at least one elastic region of the cover element functions as a reset element.

8. The speech valve of claim 1, further comprising: the elastic material of the cover element is a rubbery elastic material.

9. The speech valve of claim 1, further comprising: the elastic material of the cover element is a linear-elastic material.

10. The speech valve of claim 1, further comprising: the cover element is made of the elastic material.

11. The speech valve of claim 1, further comprising: the closure element comprises a rigid material.

12. The speech valve of claim 1, further comprising: the cover element extends at least in part beyond the housing part on the outside.

13. The speech valve of claim 1, further comprising: the cover element extends laterally and vertically beyond the housing part.

14. The speech valve of claim 1, further comprising: the cover element has a cervical edge.

15. The speech valve of claim 1, further comprising: the cover element has a height from the proximal end to the distal end, which is generally equal to the height of the housing part.

16. The speech valve of claim 1, further comprising: the filter is disposed in the housing part with a transition tolerance, or an excess tolerance.

17. The speech valve of claim 1, further comprising: the filter has an airtight skin, at least on its distal end, at least in sections.

18. The speech valve of claim 1, further comprising: the filter is partially compressed by the actuation of the speech valve.

19. The speech valve of claim 1, further comprising: a compression of the filter is limited by means of a counter bearing disposed on or in the housing part.

\* \* \* \* \*